(12) United States Patent
Viel et al.

(10) Patent No.: US 6,720,192 B1
(45) Date of Patent: Apr. 13, 2004

(54) SCREENING FOR ANALYTES USING LABELED RECEPTORS

(75) Inventors: Gerhard Theodoor Viel, Groningen (NL); Kornelis Ensing, Roodeschool (NL)

(73) Assignee: Merska B.V., Groningen (NL)

( * ) Notice: Subject to any disclaimer, the term of this patent is extended or adjusted under 35 U.S.C. 154(b) by 0 days.

(21) Appl. No.: 09/830,543

(22) PCT Filed: Oct. 30, 1998

(86) PCT No.: PCT/NL98/00629

§ 371 (c)(1), (2), (4) Date: May 9, 2001

(87) PCT Pub. No.: WO00/26674

PCT Pub. Date: May 11, 2000

(51) Int. Cl.[7] .................... G01N 33/567; G01N 33/533; G01N 33/534; G01N 33/535

(52) U.S. Cl. ...................... 436/503; 435/7.93; 436/504; 436/526; 436/527; 436/530; 436/531; 436/534; 436/535; 436/545; 436/546; 436/815; 436/817; 436/829

(58) Field of Search ................................ 436/534, 531, 436/829, 527, 526, 817, 530, 815, 545, 546, 503, 504, 535; 435/7.93

(56) References Cited

U.S. PATENT DOCUMENTS 4,978,625 A    12/1990   Wagner et al.

FOREIGN PATENT DOCUMENTS

| WO | WO 9310226 | 5/1993 |
| WO | WO 9739736 | 10/1997 |
| WO | WO 9819166 | 5/1998 |

OTHER PUBLICATIONS

Copy International Search Report.
Viel, Gerhard T. et al. "Size–exclusion chromatographic reconstruction of the bovine brain benzodiazepine receptor. Effects of lipid environment on the binding characteristics" J. Chromatogr., A (1997) 776(1), 101–10 Coden: JCraey; ISSN: 0021–9673m XP002108060.
"Phospholipids" Molecular Probes, Product Information, Jun. 16, 1999, pp. 1–4, XP002108061.

*Primary Examiner*—Mary E. Ceperley
(74) *Attorney, Agent, or Firm*—Kirkpatrick & Lockhart LLP; Anthony H. Handal

(57) ABSTRACT

A method for assaying an analyte in a sample. The method comprising the steps of a) contacting the sample with material comprising a receptor which is present in a liposome and which liposome comprises a detectable functionality, said contact occurring under conditions resulting in binding of the receptor to analyte if present before or concomitant with step b, wherein step b) consists of contacting the sample with an immobilised ligand for the receptor said contact occurring under conditions resulting in binding of the receptor to the ligand, with steps a and b being followed by c) separating the resulting immobilised ligand-receptor fraction and the receptor fraction present in solution and d) assaying the detectable functionality of the receptor in a fraction from step c) in a manner known per se for its detection. Suitably the receptor is being present in step a) in a concentration between 1 pM–1 nM and the detectable funcitonality in step a) is present in a concentration of 1 pM–1'1 M and the immobilised ligand in step b) having a Kd for the receptor <50 nM. The immobilised ligand should be present in an amount required to capture 10–99% of the receptors in the assay in the absence of analyte at a receptor concentration below the Kd of the immobilised ligand and receptor under conditions otherwise corresponding to those of the assay. The conditions and the detectable functionalities being selected such that a 0.1–10% change in either the ligand-receptor fraction or in the free receptor fraction can be qualitatively or quantitatively detectable.

30 Claims, 5 Drawing Sheets

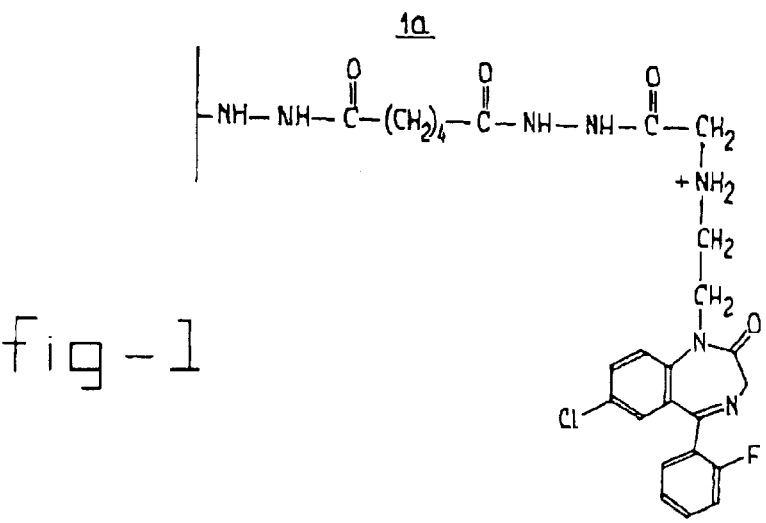
A) IMMOBILIZED DIDESETHYLFLURAZEPAM
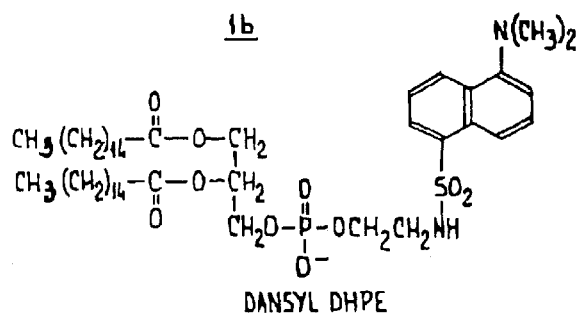
DANSYL DHPE
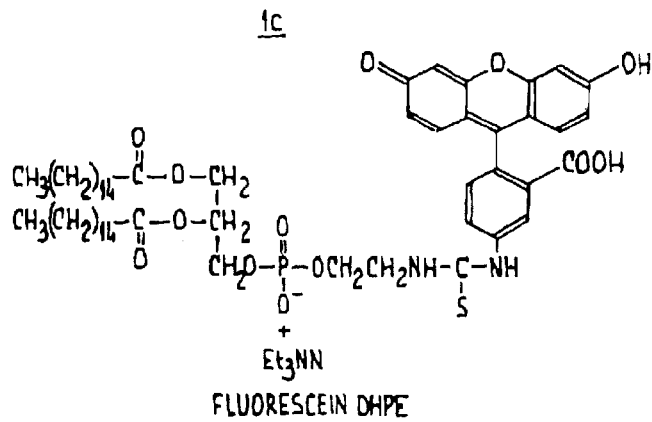
FLUORESCEIN DHPE
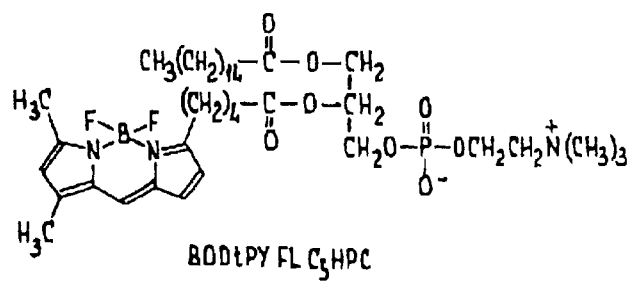
BODIPY FL C$_5$HPC
fig-1

Fig-2
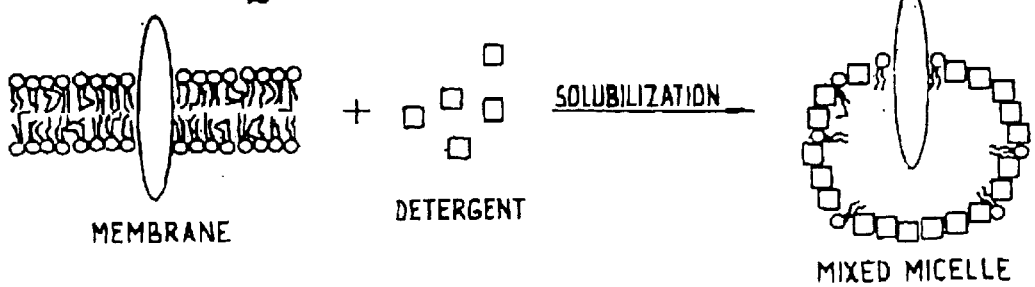
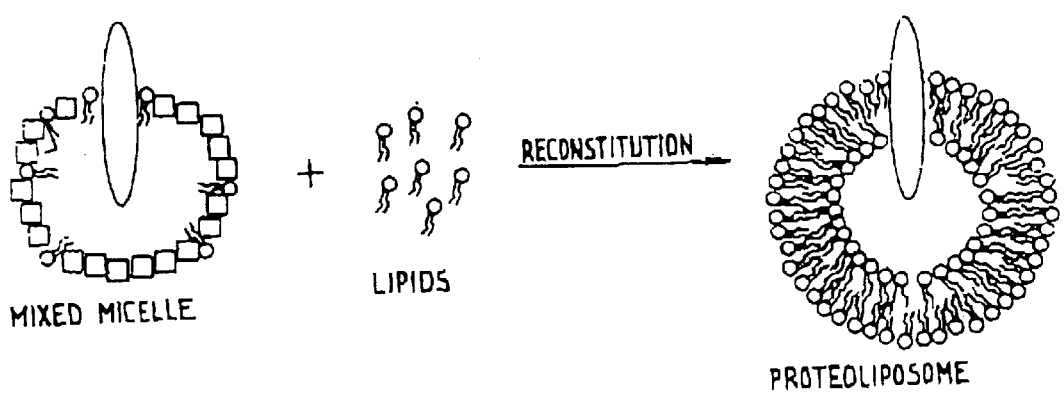
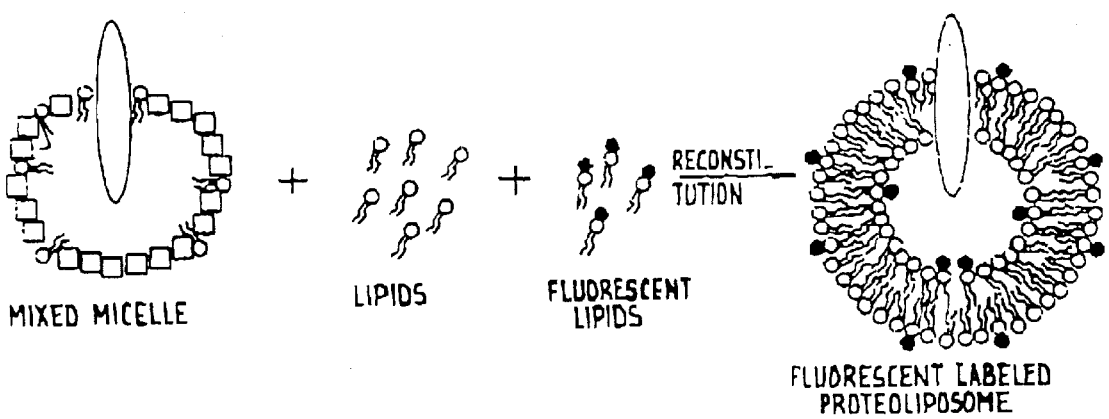
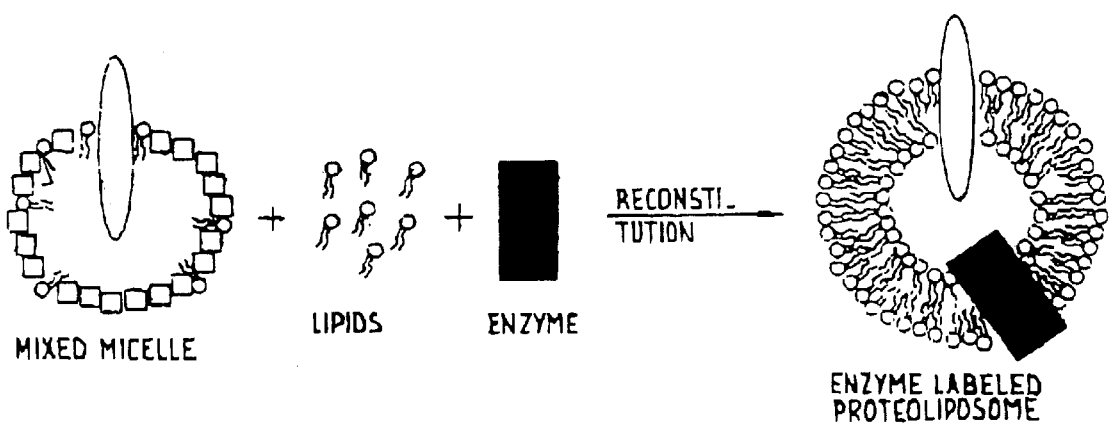

fig-3

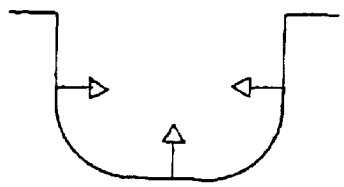

MICROTITERPLATE CONTAINING IMMOBILIZED LIGAND

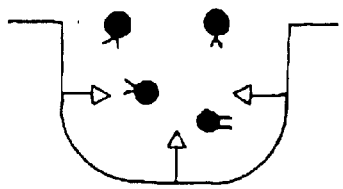

ADDITION OF PROTEOLIPOSOMES CONTAINING RECEPTOR PROTEINS AND FLUORESCENT LIPIDS

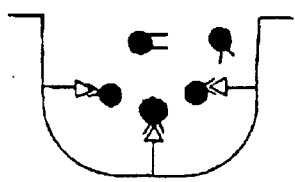

ADDITION OF ANALYTE

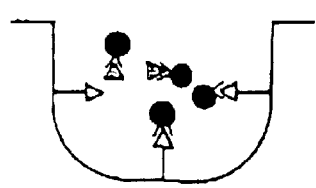

COMPETITION BETWEEN ANALYTE AND IMMOBILIZED LIGAND FOR THE SAME RECEPTOR BINDING SITE

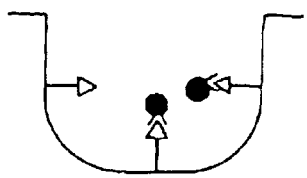

AFTER WASHING FLUORESCENCE CAN BE DETERMINED IN THE WELL AND IS A MEASURE FOR THE AMOUNT OF ANALYTE THAT WAS PRESENT IN THE SAMPLE

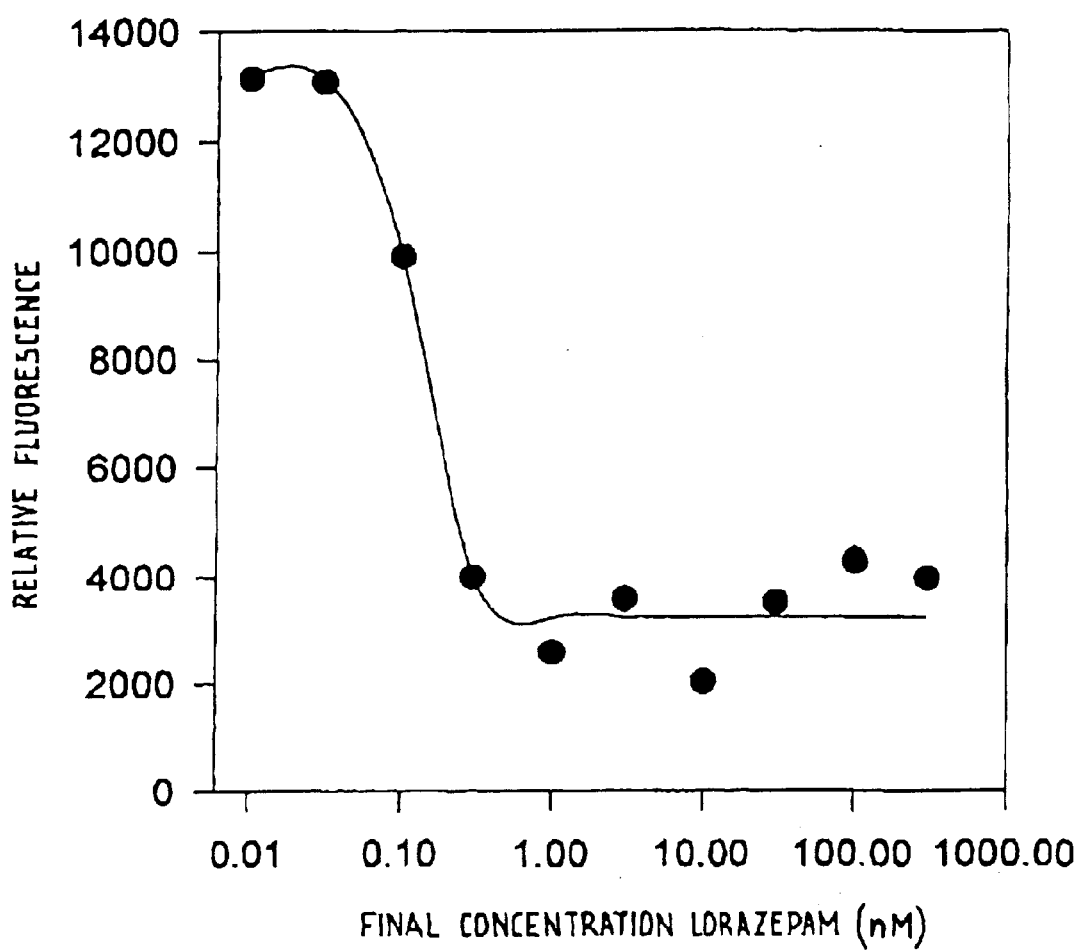

SCREENING FOR ANALYTES USING LABELED RECEPTORS

INTRODUCTION

Receptor binding assays have been commonly used for the assessment of the pharmacological properties of New Chemical Entities (NCE). Due to the introduction of combinatorial chemistry in the pharmaceutical industry, in an attempt to find succesful drug candidates, an enormous increase in NCE requires a concomitant demand for high through-put screening systems. Due to their specific properties receptor assays have been considered valuable analytical tools for the quantitation of highly potent drugs that exert their pharmacological action via a receptor interaction.

The term receptor is exclusively used for proteins which can interact with hormones, neurotransmitters and drugs or poisons yielding or blocking a pharmacological response. Thus therefore antibodies, circulating or membrane bound proteins e.g. enzymes cannot be considered receptors even if they should have ligand binding properties.

The principle of receptor binding assays is based on the competition between a ligand and an analyte for binding to a certain receptor. After incubation of ligand, analyte and receptor followed by separation of the receptor bound and the free fraction of the ligand by either filtration, centrifugation or dialysis, subsequently one or both resulting fractions are quantitated. The subsequently acquired data can be used for assessment of the affinity of a NCE for the receptor or for quantitation of a particular receptor binding analyte.

Up till now, all receptor assays have been construed around the use of a (radio) labeled ligand. Furthermore generally receptors present in animal tissue or cultivated cell lines have been used after having undergone only little purification. Typical receptor densities in commonly used receptor assays range from 10–100 picomole per gram tissue. This subsequently implies that the amount of displaceble labeled ligand in such assays is limited. The use of radioactive ligands in such cases is notwithstanding this attractive because radioactivity can be detected with good sensitivity and limited back-ground signals from such receptor material. Another important reason in favor of use of radioactive labels is that development is easy once a compound has been identified that binds to a particular receptor with high affinity. Replacing 1–6 hydrogen atoms by the same number of tritium atoms yields a product that has a receptor affinity similar to that of the unlabeled ligand. However disadavantages such as the limited shelf-life and the problems encountered with the use of radioactive tracers has stimulated the search for alternatively labeled ligands. Another motivation for such search was also the expectation that alternative labels might improve the sensitivity of the assay with regard to limits of quantitation. Taken into consideration the physical half-life and the counting time of each sample it can be calculated for tritium by way of example that only 1 out of each million labeled molecules is detected.

Almost all approaches with non-radioactive labeled ligands have been with fluorescent labels. The development of fluorescent ligands with a high receptor affinity, if the ligands itself does not have sufficient native fluorescence, is quite difficult and a compromise between affinity and fluorescence properties has always been required. The aforementioned low receptor density implies that the maximal signal is limited and lies close to the limitations of available instrumentation. High amounts of receptor containing material needs to be used per assay in order to sufficiently increase the signal.

Furthermore the currently used receptor containing materials in receptor assays contain large amounts of non-receptor proteins which cause a high fluorescence background.

Time-resolved fluorescence or fluorophores that emit at wavelengths >500 nm could partially solve this problem but provides no real break-through. In patent application PCT/NL96/00418, Janssen et al. have reviewed the existing literature on assays and recognized these problems. The review is incorporated herein by reference. Janssen et al subsequently modified the procedure to quantitate the bound fraction of labeled ligand after dissociation of the labeled ligand from the receptor which took place after the separation of the bound and free fractions of the labeled ligand. Initially they developed a fluorescent labelled benzodiazepine receptor ligand attempting to obtain a homogeneous assay using polarisation fluorescence.

The adapted procedure with the dissociation step opened a new array of detection modes for the ligand. Principally if a high affinity receptor binding compound has unique physico-chemical properties e.g. halogen atoms which can be detected with gas chromatography with electron capture detection, it can be used as a ligand in such a receptor assay.

It can be concluded that the development of non-radioactive labeled ligands is difficult because the bulky groups, required to obtain e.g. highly fluorescent probes that emit at higher wavelengths at the same time reduce the receptor affinity of the product. Furthermore a further disadvantage is that per ligand-receptor interaction only one detectable functionality is present.

Benzodiazepine receptors in particular remain important in clinical pharmacology because of their widespread use. Benzodiazepines are extensively metabolized yielding a range of active and inactive metabolites. The overall effect of a benzodiazepine can therefore not be properly related to the concentration of only the parent drug. Quantitation of the individual compounds, parent drug and metabolites on the other hand is highly impractical and assays that could measure the sum of all active compounds could be beneficial.

To solve such a problem an immuno assay could be used, However the affinity of the individual compounds towards the applied antibody does not correlate with the affinity of these individual compounds towards the receptor. This thus precludes the measured response being a proper reflection of the total pharmacological effect. It is for this reason that the use of the receptor which mediates the pharmacological effect in an assay forms a logical step.

Traditional receptor assays using radioactive or non-radioactive ligands require a separation step enabling quantitation of bound and or free fractions of the labeled ligand. Procedures used for the separation are dialysis, centrifugation and filtration. The selection depends on available instrumentation and equilibrium dissociation constants of the labeled ligand and of the analyte. It is a requirement that the separation step may not alter the amount of receptor bound ligand.

Dialysis is a slow process, up to 24 hours. Automation is cumbersome because collection of the fractions containing the bound plus free and the free fraction of label and analyte is hardly possible. In addition miniaturisation is precluded.

Centrifugation with or without precipitation of the labeled ligand or the soluble or solubilized receptor has limited applicability for receptor assays because the separation process can change the bound fraction of the labeled ligand. Moreover it is difficult to quantitatively collect sedimented receptors. Automation of centrifugation steps also remains problematic. Filtration is the method of choice albeit that due to the amounts of receptor containing tissue per sample minimal filter surface areas are required. This is to avoid clogging of these filters and to warrant accurate quantitation of the bound fraction of the labeled ligand. There are a number of filtration devices (Skatron, Brandell, Millipore) that allow parallel filtration of up to 96 samples. It should be noted however that filtration capacity per filter is limited and that the precision of the methods is strongly dependent on the differences in filtration rate between the individual filters. With the exception of the Millipore system it is not possible to collect either the free fraction of the labeled ligand or the bound fraction of the labeled ligand after dissociation from the collected receptor fraction.

It is an objective of the subject invention to provide a highly sensitive receptor-ligand assay that allows miniaturisation and automation to be suitable for high through-put purposes. The assay should preferably be amenable for non-radioactive ligands. The specific materials of the assay, being the main ingredients of a kit, should be available in adequate quantities and show controllable batch to batch variations. Such an assay must be simple to execute and economically feasible enabling routine laboratory application.

SUMMARY OF THE INVENTION

The subject invention provides a highly sensitive receptor assay that does not require ligands with a detectable label but provides a test with at least the sensitivity and specificity of radioactive receptor assays. Such an assay according to the invention is simple to execute and economically feasible enabling routine application. Also a combination of immobilised ligand and a labeled receptor preparation suitable for use in an assay according to the invention is provided. Quite specifically an assay for benzodiazepine detection and quantitation is provided. Suitably a benzodiazepine sensitive receptor will be used.

DESCRIPTION OF THE INVENTION

The subject invention provides a method for quantitatively and/or qualitatively assaying an analyte in a sample, said analyte being a receptor binding compound. In an assay according to the invention the receptors of interest can originate from receptor containing tissue of animal source such as in vitro cultures of animal cells or tissues or from microorganism cultures. The method has low detection limits equivalent to those of traditional receptor assays that employ labeled ligands. The method comprises the steps of a) contacting the sample with material comprising a receptor which is present in a liposome and which liposome comprises a detectable functionality, said contact occurring under conditions resulting in binding of the receptor to analyte if present before or concomitant with step b, wherein step b) consists of contacting the sample with an immobilised ligand for the receptor said contact occurring under conditions resulting in binding of the receptor to the ligand, with steps a and b being followed by c) separating the resulting immobilised ligand-receptor fraction and the receptor fraction present in solution and d) assaying the detectable functionality of the receptor in a fraction from step c) in a manner known per se for its detection. In a suitable embodiment the receptor is present in step a) in a concentration between 1 pM–1 nM. The detectable functionality in step a) is suitable present in a concentration of 1 pM–1 µM. The said immobilised ligand in step b) suitably has a Kd for the receptor <50 nM.

The method according to the invention is suitable for automation allowing high through-put of samples.

Liposome is an art recognised term and refers to particles capable of maintaining their basic structural integrity in an aqueous environment. They are formed from amphipathic molecules with hydrophilic surfaces that are exposed to an inner aqueous space and also to surrounding aqueous medium. They can also be called multilamellar vesicles which are comprised of multiple concentric layers of lipid. Numerous methods are described in the art for making liposomes. In summary a known process for example as disclosed in U.S. Pat. No. 4,235,871 comprises preparing and mixing a solution of lipid to be deposited in an organic solvent, followed by evaporating the solution to dryness to produce a thin lipid film on a glass vessel followed by hydration and liposome formation by vortexing or in any other mechanical means in an appropriate buffer. The resulting structure is such that the hydrophilic heads are orientated outwards toward the aqueous medium and the hydrophobic structure is oriented inwards. Further purification is possible for example by column chromatography. Alternative methods are disclosed in U.S. Pat. Nos. 5,017,501 and 5,094,785. The cited documents are incorporated by reference and serve merely as examples of possible ways to manufacture liposomes. Alternatives are available to the person skilled in the art and such methods are also to be considered incorporated.

Suitably the immobilised ligand will be used in the method in an amount required to capture 10–99% of the receptors in the assay. This amount is the amount required in the absence of analyte and at a receptor concentration below the Kd of the immobilised ligand and receptor under conditions otherwise corresponding to those of the assay. A method according to any of the embodiments of the invention can suitably use an immobilised ligand that is a structurally related analog of a compound with affinity towards the receptor of interest which is coupled directly or coupled via a spacer arm to the surface of a carrier material. In the event of a spacer being applied this will usually have a length of between 5–20 carbon atoms preferably of 10–15.

The conditions of the assay and the detectable functionality are selected such that a 0.1–10% change in either the ligand-receptor fraction or in the free receptor fraction can be qualitatively or quantitatively detected. A method according to the invention thus suitably uses an amount of immobilised ligand per assay, between 0.5 femtomole and 0.5 nanomole. When the ligand bound fraction of the receptors is quantitated, dissociation of the receptor from the immobilised ligand may be required. The selection of the detectable functionality and its quantitation in either the free or ligand-bound fraction determines whether the functionality can be detected itself, or whether the functionality is such that it is degraded completely and uniformly thereby yielding a detectable product, or whether the functionality converts a further molecule into a detectable product. Suitably detection can occur after mixing reagents with the liposomes to enable the incorporated detectable functionalities (e.g. enzyme) to produce a readily detectable product. Alternatively the free fraction of liposomes containing the receptor of interest and the detectable functionalities are transferred into a container or detection cell. There they can either be readily detected or be subjected to further treatment leading to production of detectable product. In a method according to the invention it is preferable the receptor material and the immobilised ligand release no interfering compounds during the incubation or during the quantitation of the detectable functionalities. Also in a method according to any of the preceding claims the conditions are preferably chosen to ensure the stability of the detectable functionality and dependent on the detection mode also the stability of the detectable product.

The steps a and b can be carried out concomitantly. The sensitivity of the method can however be improved by carrying out step a) prior to step b) in order to enable establishment of controlled non-equilibrium thus providing greater sensitivity. Low concentrations of immobilised ligand and labeled receptor can also improve the sensitivity, particularly for high-affinity ligands with $K_d$ below 10 nM. In a suitable embodiment of the method acording to the invention the number of detectable functionalities is 1–10000 times the number of receptors. Also in a suitable embodiment of the invention the detectable functionality for example an enzyme is able to produce a detectable product in a number between 10–1000000 times the number of receptors.

In particular the method according to the invention is directed at carrying out assays wherein the analyte is to be detected at a level of 1 $\mu$M, preferably below 0,5 micromolar level. The assay can also even be carried out successfully on analyte levels below 100 nM, even below 50 nM. Preferably the invention is carried out to ascertain levels as low as possible. With a view to developing potent drugs and analysis of their activity levels analyte concentations as low as 1 picomolar but also as low as 100 femtomolar are of interest, The method is applicable to use on analyte containing samples of less than 1 ml, preferably even less than 250 $\mu$l. In a suitable embodiment of the invention the method takes place in assay volumes between 1 and 250 $\mu$l. Preferably the method according to the invention is carried out in volumes as small as 10 $\mu$l but also samples as low as 1 $\mu$l are of interest.

In a method according to the invention a suitable embodiment comprises adding labeled receptor in an amount equivalent to a concentration within the range $0.001-1*K_d$ of the receptor and the immobilised ligand. Preferably the receptor is added in a concentration between 0.01 and $0.5*K_d$. Quite suitably a concentration of approximately $0.05*K_d$ is applied. For a large number of ligands $K_d$ values are already available from handbooks. A person skilled in the art can also ascertain in a manner known per se what the $K_d$ value is for a particular ligand and receptor. In general an immobilised ligand with a $K_d$ below 50 nM, preferably below 10 nM, is an excellent candidate for use in the assay according to the invention. Such a $K_d$ ensures the required sensitivity for detecting and quantifying trace amounts of analytes or receptors.

The constitution of the receptor preparation is adapted to this alternative method set-up. Most receptors in their native form are imbedded in cell membranes in a manner which warrants their ligand and analyte binding ability. A receptor preparation as used in traditional receptor assays consists of homogenized tissue, rich in the receptor of interest, which is fractionated by centrifugation to remove cell nuclei, soluble proteins and unhomogenized fragments. This preparation consists of membrane fragments in size ranging from 0.1–5 $\mu$m and further containing a highly variable number of receptors per fragment. For the method according to the invention more uniform material labeled with a detectable functionality is required. To arrive at such material proteins including the receptor protein in membrane fragments are solubilized for example by addition of detergents. The resulting solubilized receptors can then be purified by affinity chromatography which results in fairly unstable product. Addition of an excess of selected lipids to solubilised receptor will lead to the formation of liposomes and reconstitution of the solubilized (receptor) proteins. This means the receptor protein is incorporated in liposomes like the receptor protein is incorporated in membrane fragments. This procedure thus restores binding properties of the receptor protein and also warrants receptor stability. Functionalities required for the detection of the receptor must also be incorporated in the liposomes. The functionalities can be modified substituents of the liposome itself, e.g. lipids or lipid like molecules to which a detectable functionality is coupled. Alternatively the functionalities can be proteins or protein like, molecules that are themselves reconstituted in the liposome like the receptor protein.

The simplest way to introduce detectable functionalities into the receptor comprising liposome is by adding them to the solubilized receptor preparation prior to the addition of the lipids required for the reconstitution. Alternatively liposomes containing the reconstituted receptor can be mixed with liposomes containing the detectable functionalities. Fusion by freeze-thawing cycles and/or sonication of the different types of liposomes can subsequently yield the labeled receptor containing liposomes. (Ref.: MacDonald).

The solubilisation of receptors and the reconstitution of the solubilized receptor into liposomes and the labeling of the receptor containing liposomes can be carried our in a number of manners. Each receptor will require its own set of reagents and procedures to maintain or restore the native binding properties of the receptor.

In the method according to the invention step c) can be carried out in a number of manners which will be apparent to a person skilled in the art It will depend on the, nature of the carrier material with the immobilised ligand whether additional pretreatment steps prior to separation are required. The simplest way of carrying out step c) comprises emptying and optionally rinsing containers, i.e. tubes or microtitre plates to which the ligand is coupled e.g to the inside wall. Either the free fraction of labeled receptors in the solution or the bound fraction of the labeled receptor remaining in the container can be measured.

The carrier material on which the ligand is immobilised can include the walls of test tubes or microtitre plates, beads, nitrocellulose, membranes, latex microparticles, glass metal or gel. Polystyrene and polypropylene are suitable materials. The exact material is not critical. The requirement is that the ligand can be immobilised on such carrier material. The immobilisation encompasses all mechanisms for binding the ligand to the solid carrier such that during the assay the ligand remains fixed to the carrier. Such mechanisms can comprise covalent or non covalent binding, absorption by ionic interactions, hydrophobic/hydrophobic or hydrophilic/hydrophylic, interactions.

In an embodiment whereby the bound fraction of the labeled receptor is retained by immobilised ligands on the surface of a well of a container e.g. a microtitre plate the amount of receptor material must be such that in the absence of analyte between 10 and 99% of the labeled receptor can be bound to the surface. By way of example the amount of labeled receptor material can be less than 0.1 pmole when the assay volume equals 250 $\mu$l as is the case when using 96 well microtitre plates. Quite suitably in general the amount of receptors used per assay can lie between 1 femtomole and 1 picomole. The detection can occur for example by adding reagents to the liposomes bound by the immobilised ligands to enable the incorporated detectable functionalities (e.g. enzyme) to produce a readily detectable product. Where bound fraction is to be detected the free fraction can be suitably transferred to waste. This can ocur with or without additional washing steps of the container with the liposomes bound to the immobilised ligands. Suitably in any case the liposomes with the detectable functionality are dissolved in a medium allowing quantitation of the functionality in a manner known per se for said functionality.

The method according to the invention can be carried out using membrane bound receptors as illustrated for the benzodiazepine receptor, which are solubilized and reconstituted in liposomes. Alternatively a receptor of interest can be a soluble receptor which is isolated and subjected to a labelling process. Suitably the soluble receptor is selected from the following group: steroid hormone, androgen, estrogen and progesteron receptors. Suitably liposomes according to the invention also contain labeled lipids (e.g. fluorescent) as detectable functionality. Any of the embodiments described for the invention can be applicable for a benzodiazepine receptor based assay. A benzodiazepine based assay is not restricted to the parameters and variables as disclosed merely in the example. In such an assay the ligand can suitably be a benzodiazepine derivative. A large number of such compounds are available for use in the assay and are well known to the person skilled in the art. Suitable examples of the receptor of interest being a membrane bound receptor can be selected from the following group: adenosine, adrenergic, dopamine, histamine, muscarinic (or acetylcholinergic), nicotinic, opiate, serotonin, benzodiazepine, GABA, glycine, calcium channel, sodium channel, chemotactic peptide, epidermal growth factor, glucocorticoid, cannabinoid, cholecystokinin, cytokines, leuktriene and neurokinin receptors. Receptors that are soluble by nature can be incorporated directly in liposomes.

It is commonly known that ligand receptor binding can be very sensitive to structural modifications of the ligand as was observed for the development of fluorescent labeled ligands for e.g. the benzodiazepine receptor as reported by Janssen et al Generally the label is linked via a spacer to a compound with affinity for that receptor or a closely related analog thereof. The impact of the size of the fluorophore being used as label on the binding is much larger than the impact of the spacer alone. In the present approach the ligand can be coupled via a spacer to a rather inert carrier material e.g. the modified surface of a container e.g. a microtitre plate. The most favorable location for such linkage and also places impossible for such linkage have been assayed in the prior art for numerous ligands. Naturally for application in the subject method the ligands should only be considered with a spacer in such a favorable location. In general when using a spacer linking the ligand with the carrier material, the spacer will comprise a carbon chain of between 5–20, preferably 10–15 carbon atoms. The general requirements for the detectable ligand have been summarized elsewhere in the description of the method according to the invention.

The suitable ligands and spacers can be determined by the person skilled in the art using details readily available concerning affinities and receptor structures. We illustrate this for the immobilised ligand for the benzodiazepine receptor. A number of suitable immobilised ligands already exist and naturally it is possible to prepare numerous immobilised ligands on the basis of the information presented in the subject application which can be suitably applied in the subject invention. Preferred immobilised ligands will be those described in literature. We provide an example of an immobilised ligand that can be readily produced. We also refer to publications of Sigel and Taguchi which illustrate the preparation of immobilised ligands.

In the method according to the invention a ligand was linked to a spacer and subsequently to a reactive group attached to the surface of the container e.g. microtitreplate. The spacer used comprised an amino group The receptor preparation used was prepared by first subjecting a purified and lyophilized membrane fraction to a treatment with deoxycholate under well-defined conditions to minimize loss of active receptor binding sites. By centrifugation or membrane filtration the solubilized material could then be separated from the remainder of the membrane fraction. The next step was the reconstitution of the solubilized receptor by the addition of asolectin. Other lipids, alone or in combination can also be be used to yield comparable products. In a method according to the invention the receptor material, used for solubilisation can be a P2-pellet derived from receptor containing tissue. Such a P2-pellet may suitably have a receptor concentration of 0.5–5 picomole/mg protein. The P2-pellet can be solubilized with a detergent or a mixture of detergents, said detergent suitably being selected from the following group: salts of anionic detergents, cationic detergents, zwitterionic detergents and nonionic detergents. The reconstitution of solubilised receptor material can occur with lipids suitably selected from the following group: phospholipids, glycolipids and cholesterol.

Theoretically a large variety of detectable functionalities can be used in combination with a technique or procedure that can be used for selective and sensitive quantitation. Considering one particular intended application of the method the quantitation technique or procedure should be fast, rugged, cost-effective and applicable to small sample volumes and be amenable to automation.

Radiolabels, preferably $^3$H or $^{125}$I, attached to the constituents of the liposomes e.g. the lipids, remain attractive as a form of label to be used in the method according to the invention. This is because a large number of labels per liposome or per receptor binding site can be obtained. Moreover quantitation of bound or free fractions of radioactively labeled liposomes is simple and reliable. In addition considering the availability of multi-channel detectors high through-put can be warranted. However, wide-spread use of this radioactive variation is limited because of legal limitations in the use of radioactive substances and the disposal of radioactive waste. Thus non radioactive functionalities are also of eminent importance as they have more potential in practical terms.

Functionalities that can readily be detected with spectroscopic, preferably fluorescent or chemi-luminescent, techniques thus have a better practical potential. In contrast to traditional receptor assays in which fluorescent labeled ligands are used, the selection of the fluorophore in the method according to the invention is not affected by a possible effect on the receptor binding properties. Thus any fluorophore with favorable spectroscopic properties can be used. Favorable spectroscopic properties are an emission wavelength and preferably an excitation wavelength of the fluorophore longer than 500 nm in order to limit background fluorescence caused by membrane proteins that are also reconstituted in the liposomes. Selected fluorescent labeled lipids, as depicted in FIG. 1 were mixed with the lipids used for the reconstitution process. Between 0.1 and 2% of all lipids contained a fluorescent label and provided good results. With increasing label concentrations some quenching was observed however the highest labeling density yielded the highest fluorescent signal.

A different type of detectable functionality that offers new opportunities for reduction in sample size and improvement of method sensitivity is formed by the group consisting of enzymes. Enzymes that can be incorporated in liposomes containing the receptor of interest can be used to amplify the signal by converting a precursor into a spectroscopically detectable product, preferably of fluorescent or chemiluminescent nature. An assay based on luciferase appears to have high potential in that only an increase in signal and virtually no back-ground signal is detected. Alternatives that are suitable as well are by way of example detectable functionalities selected from alkaline phosphatase and monoamine oxidase. Illustrative examples of the labels mentioned are known in the art and can also be selected from pigments, dyes, stable free radical luminescents etc.

The selection of lipids for the reconstitution of solubilized receptors is not very critical and can be done by a person skilled in the art. The selection of detectable functionalities can be done by a person skilled in the applied detection technique implying knowledge of the physico-chemical characteristics of the functionality and tuning of the detection to optimize signal to noise ratios. The same detectable functionality can be used for any receptor under the condition that the receptor and the detection to optimize signal to noise ratios. The same detectable functionality can be used for any receptor under the condition that the receptor and the detectable functionality can be both reconstituted in the same lipid mixture or that liposomes containing either the receptor or the detectable functionality can be fused e.g. by freeze-thawing cycles and/or sonication, yielding liposomes containing both entities.

Where different receptor types are simultaneously used in one test, liposomes containing different receptors and different labels are to be used. Thus each liposome type comprises only one receptor type and different immobilized ligands.

The detectable functionality in the example provided of the method according to the invention is fluorescein labeled-DHPE. This was added in an amount of 0.3% relative to the amount of asolectin used for the reconstitution. In the method the liposomes containing the benzodiazepine receptor and fluorescein labeled DHPE preferably bind to the immobilised ligand and do not bind to the surface of the microtitre plate. Suitable detectable functionaliuties are well known in the art. They can by way of example be selected from the group consisting of dansyl DHPE (dansyl-dihexadecanoylphosphatidylethanolamine), fluorescein DHPE and bodipy $FLC_5HPC$ (beta-BODIPY labeled pentanoyl-1-hexadecanoylphosphatidylcholine). The measured signal of the detectable functionalities in the liposomes changes with the concentration of analyte present in the sample. It should be noted that the analyte will only affect the fraction of the liposomes bound to the immobilised ligand and not the liposomes that are non-specifically bound to the surface of the microtitre plate. The latter fraction in general should be substantially smaller than the first fraction to warrant substantially the precision of the method. In the method in the example no additional measures were take to reduce non-specific binding of the liposomes to the surface. The procedure can however be improved by reducing non-specific binding. Different procedures to reduce non-specific binding are known to a scientist, skilled in the art The selection of the microtitre plate material, coating of the surface, addition of competing reagent in the incubation medium, washing procedures, or combinations thereof are factors that can help to reduce non-specific binding. As an alternative to the exemplified procedure the unbound fraction of labeled liposomes can be quantitated.

A kit for carrying out a method according to the invention is also envisaged as falling within the scope of the invention, said kit comprising a combination of components for carrying out the method or for making the components required for carrying out the method as detailed in the above. Thus a kit according to the invention can comprise a ligand optionally immobilised on carrier material e.g. a reaction container in which the method is to be carried out and a liposome containing receptor for binding the ligand incorporated therein. The kit can further comprise the detectable functionality either incorporated in the receptor containing liposome or in another liposome. A kit according to the invention may further comprise any of the following components reagent for the assay and/or for quantitation of the detectable functionality, calibration standard and quality control sample.

BRIEF DESCRIPTION OF THE DRAWINGS

FIG. 1 shows the chemical structures of some compounds that can be used for a benzodiazepine receptor assay according to the invention;

FIG. 2 is a schematic representation of several processes that can be employed for the preparation of proteoliposomes useful in practicing the invention;

FIG. 3 is a schematic presentation of a receptor competition assay according to the invention;

FIG. 5 illustrates a calibration curve of relative fluorescence plotted against final concentrations of a competitive ligand, Lorazepam.

Figure 4:
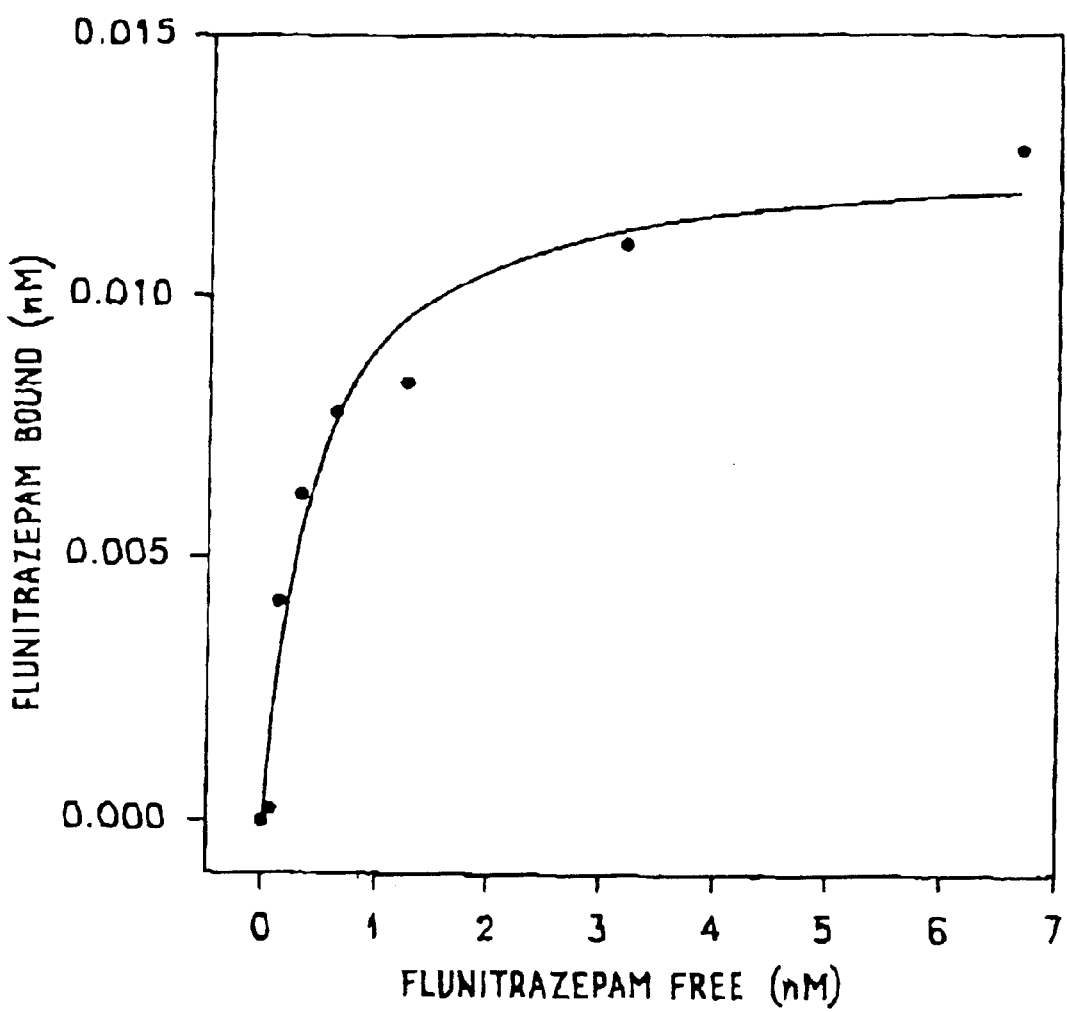
FIG. 4 plots the concentration of liposome bound flunitrazepam as a function of the concentration of free tritium labeled flunitrazepam.

The drawings illustrate, in a schematic manner, some exemplary methods of the invention and of the results obtainable, one example of which is described in more detail hereinafter. Many of the relevant details of these methods and results are apparent from the drawings and the legends thereon or from the example which follows the description of the drawings.

The structure shown in FIG. 1, are, as labeled those of immobilized didesethylflurazepam (subfigure FIG. 1a) and the fluorescent detector functionalities, dansyl DHPE (subfigure FIG. 1b), fluorescein DHPE (subfigure FIG. 1c) and bodipy $FLC_5HPC$ (subfigure FIG. 1d).

Referring to FIG. 2, the methods shown comprise, in the first line, the solubilization of membrane receptors with detergent to produce a mixed micelle comprising the receptor, detergent molecules and some receptor lipid fragments. The second through fourth lines of FIG. 2 show the reconstitution of the mixed micelle with suitable lipids into an unlabeled proteoliposome (second line), and additionally with fluorescently labeled lipids to form a fluorescent labeled proteoliposome (third line) or an enzyme labeled proteoliposome (fourth line).

Referring to FIG. 3, the competition receptor assay shown uses an immobilised ligand attached to a microtiter plate and receptors embedded in liposomes containing a detectable fluorescent functionality. Proteoliposomes containing receptors an fluorescent marked lipids are added to the microtiter plate followed by analyte, enabling competition between the analyte and ligand for the receptor binding sites. After washing measurement is made of the bound fraction of receptors attached to the ligand immobilized in the microtiter plate from which the analyte may be quantified by calculation.

To obtain the data shown in FIG. 4, the free fraction of proteoliposomes is collected and incubated with a fixed concentration of tritium-labeled flunitrazepam. The curve shows the binding of non-labeled liposomes containing reconstituted benzodiazepine receptor versus the immobilised ligand as a function of the concentration of analyte, tritium-labeled flunitrazepam. The benzodiazepine receptor is produced by the process shown in FIG. 2.

To obtain the data shown in FIG. 5, a fixed amount of receptor-containing, fluorescent labeled liposomes are incubated with a fixed amount of immobilised ligand in the presence of increasing concentrations of a competitive ligand, Lorazepam.

EXAMPLE

Preparation of Immobolized Benzodiazepine Containing Microtiter Plate and Development of a Nonisotopic Receptor Assay using Fluorescent Proteoliposomes 1. Description of the Method A benzodiazepine (didesethylflurazepam) was immobilized on a 96-well microtiter plate via a hydrophilic spacer of 15-atom length, three of which originate from the benzodiazepine itself. The benzodiazepine receptor was solubilized from bovine brain tissue and reconstituted into proteoliposomes using asolectin (soybean lipids) as additional lipid source and fluorescein-DHPE as labeled (fluorescent) lipids. The fluorescent proteoliposomes bound to the immobilized benzodiazepine and were displaced by increasing amounts of free benzodiazepine (analyte) in the sample. Additionally, saturation binding experiments were done with [$^3$H]flunitrazepam on unlabeled proteoliposomes after binding to the immobilized ligand with increasing amounts of radioligand.

2. Materials and Methods

Preparation of Microtiter Plate Containing Immobilized Benzodiazepine

200 μl 0.5 M adipic acid dihydrazide (pH 7.5) was added to each well of a Reacti-Bind™ maleic anhydride activated polystyrene 96-well microtiter plate from Pierce (Rockford, Ill., USA) and incubated for 48 h at 35° C. The plate was washed twice by rinsing the wells with distilled water. Incubating the wells with 200 μl 1 M 2-aminoethanol (pH 7.5) for 1 h at 35° C. blocked excess reactive sites on the plate. The plate was washed with distilled water, 1 M NaCl and, again, distilled water. Each well was incubated with 200 μl 30 mM sodium iodoacetate (pH 5.0) and 50 μl (from a 240 mg/ml stock solution of) 1-ethyl-3-(3-dimethylaminopropyl)carbodiimide hydrochloride (pH 5.0) for 3 h at 35° C., followed by washing twice with distilled water. 100 μl 50 mM sodium bicarbonate (pH 8.0) and 100 μl N,N-dimethylformamide, containing 0.1 mg/ml didesethylflurazepam (Ro-7-1986) was added to all wells and the plate was incubated for 48 h at 35° C., Excess reactive linker sites were blocked for 1 h at 35° C. with 200 μl 1 M 2-aminoethanol (pH 7.5) After washing three times with distilled water the plates were used immediately.

Preparation of Brain Membranes and Solubilization of the Benzodiazepine Receptor Calf brains were homogenized in 5 volumes (v/w) of ice-cold 0.32 M sucrose using a glass-PTFE Potter-Elvehjem homogenizer at 1200 rpm. The homogenate was centrifuged at 1000 g for 10 min at 4° C. The supernatant was carefully decanted and centrifuged for 60 min at 100 000 g at 4° C. The pellet was washed twice with 50 nM phosphate buffer (pH 7.4) containing 1 mM EDTA followed by centrifugation for 30 min at 100 000 g at 4° C. The final pellet was suspended in 5 volumes of the same buffer, rapidly frozen in liquid nitrogen and lyophilized for 48 h. Lyophilized membranes were suspended to a protein concentration of 8 mg/ml in ice-cold 50 mM Tris-HCl (pH 7.4, 22° C.) supplemented with protease inhibitors (1 mM benzamidine and 200 μg/ml bacitracin), 0.5 M KCl and 1 mM EDTA and were solubilized on ice by dropwise addition of 20 mg/ml deoxycholate (pH 7.6), to a final detergent concentration of 2 mg/ml. After 30 min, non-solubilized material was removed by centrifugation at 100 000 g for 1 h at 4° C. The amount of protein in the solubilized preparation was approximately 5 mg/ml.

Reconstitution of the Solubilized Receptor by Size-exclusion Chromatographic Detergent Depletion.

Soy bean lipids (asolectin) were dissolved in chloroform and subjected to rotary evaporation in a round-bottomed flask. Dissolution and evaporation were repeated twice with diethylether and the lipid film was flushed with nitrogen. The lipids were dispersed with 125 mM sodium cholate in 50 mM Tris-HCl (pH 8.0, 22° C.) to obtain a lipid concentration of 75 mg/ml (approximately 100 mM). When fluorescent proteoliposomes were made, fluorescein-DHPE was added to the dissolved soy bean lipids in chloroform and treated as described above. The concentration fluorescein-DHPE after dispersion in cholate was 250 μg/ml (⅓₀₀ part of total lipid).

A 1.5 ml aliquot of the lipid solution was mixed with 2.5 ml of deoxycholate-solubilized membranes and applied at 1.5 ml/min at 4° C. on a 39 cm×2 cm Sephadex G-50 M gel bed in 50 mM Tris-HCl supplemented with 1 mM EDTA and 0.1 M KCl. The void volume fractions containing the proteoliposomes were collected and pooled. About half of the total solubilized protein was recovered in the proteoliposome suspension.

Saturation Binding Experiment

Samples of the proteoliposome suspension containing 80 μg protein were added to the wells of the immobilized benzodiazepine microtiter plate and were incubated for 2 h at 0–2° C. with 20 μl aliquots of [$^3$H]flunitrazepam stock solutions (in 50 mM Tris-HCl (pH 7.6, 22° C.) supplemented with 1 mM EDTA) giving final concentrations of 0.1–10 nM [$^3$H]flunitrazepam. The total volume was adjusted to 200 μl with the Tris/EDTA buffer. After incubation, 150 μl samples were transferred from the wells to poly-ethylene tubes and the concentration of [$^3$H]flunitrazepam in all samples was adjusted to 10 nM and incubated further for 45 min at 0–2° C. After the final incubation, 15 μl of 33 mg/ml bovine globulins and 85 μl of a 360 mg/ml PEG-6000 solution were added. The incubation was continued for another 12 min and then stopped by the addition of 3 ml of ice-cold 50 mM Tris-HCl buffer (pH 7.6, 22° C.) supplemented with 1 mM EDTA. The mixture and two 3 ml rinsing portions of ice-cold Tris/EDTA buffer were filtered over Whatman GF/B filters, after which the filters were transferred into scintillation counting vials, shaken in a 3.5 ml scintillation cocktail for 2 h, and subjected to 5 min liquid scintillation counting.

Inhibition Experiments

Fluorescent labeled proteoliposomes samples containing 80 μg protein were added to the wells of the microtiter plate with immobilized benzodiazepine and were incubated for 2 h at 4° C. with 20 μl aliquots of lorazepam stock solutions (in 50 mM Tris-HCl (pH 7.6, 22° C.) supplemented with 1 mM EDTA) giving final lorazepam concentrations of 300 nM–30 pM. The total volume was 200 μl. After incubation the plate was washed three times with ice-cold Tris/EDTA buffer and the bound (fluorescent) proteoliposomes were measured in a fluorescence plate reader using an excitation wavelength of 496 nm and an emission wavelength of 519 nm.

References:

J. Smisterova, K. Ensing and R. A. de Zeeuw. "Methodological aspects of quantitative receptor assays" (review) J. Pharm. Biomed. anal. 12 (1994) 723–745.

M. J. Janssen, K. Ensing, R. A. de Zeeuw. Non radioactive receptor assay suitable for quantitative analysis of trace amounts of receptor binding analyte, PCT/NL96/00418.

S. Razin. "Reconstitution of biological membranes" Biochim. et Biophys. Acta 265 (1972) 241–296.

Y. Kagawa. "Reconstitution of oxidative phosphorylation" Biochim. et Biophys. Acta 265 (1972) 297–338.

J. Lindstrom, R. Anholt, B. Einarson, A. Engel, M. Osame, M. Montal. "Purification of acetylcholine receptors, reconstitution into lipid vesicles, and study of agonist-induced cation channel regulation" J. Biol. Chem. 255 (1980) 8340–8350.

M. M. Tamkun, W. A. Catterall. "Reconstitution of the voltage sensitive sodium channel of rat brain from solubillized components" J. Biol. Chem. 256 (1981) 11457–11463.

R. Anholt, D. R Fredkin, T. Deerinck, M. Ellisman, M. Montal, J. Lindstrom. "Incorporation of acetylcholine receptors in liposomes" J. Biol. Chem. 257 (1982) 7122–7134.

E. Sigel, C. Mamalaki, E. A. Barnard. "Isolation of a GABA receplor from bovine brain using a benzodiazepine affinity column" FEBS letters 147 (1982) 45–48.

J. I. Taguchi, K. Kuriyama "Purification of GABA receptor from rat brain by affinity column chromatography using a new benzodiazepine, 1012-S, as an immobilised ligand" Brain Res. 323 (1984) 219–226.

G. B. Stauber, R. W. Ransom, A. I. Dilber, R. W. Olsen. "The GABA/benzodiazepine-receptor protein from rat brain; Large-scale purification and preparation of antibodies" Eur. J. Biochem. 167 (1987) 125–133.

U. Klein, F. Fahrenholz. "Reconstitution of the myometrial oxytocin receptor into proteoliposomes; Dependence of oxytocin binding on cholesterol" Eur. J. Biochem. 220 (1994) 559–567.

M. A. Scheideler, R. S. Zukin. "Reconstitution of solubilized delta-opiate receptor binding sites in lipid vesicles" J. Biol. Chem. 265 (1990) 15176–15182.

G. Zardeneta, P. M. Horowitz. "Prospective: Detergent, liposome, and micelle assisted protein refolding" Anal. Biochem. 223 (1994) 1–6.

P. Balen, K. Kimura, A. Sidhu. "Specific phospholipid requirements for the solubilisation and reconstitution of D-1 dopamine receptors from striatal membranes" Biochem. 33 (1994) 1539–1544.

R. C. MacDonald, R. I. MacDonald. "Applications of freezing and thawing in liposome technology" in Liposome Technology (ISBN 0-8493-6707-7).

S. Siler-Marinkovic, L. Mojovic, V. Davinic, B. Bugarski. "Liposomes as carriers of antimicrobial drugs" Drug Develop. Ind. Pharm. 23 (1997) 483–488.

D. J. A. Crommelin, T. Daemen, G. L. Scherphof, M. H. Vingerhoeds, J. L. M. Heeremans, C. Kluft, G. Storm. "Liposomes: vehicles for the targeted and controlled delivery of peptides and proteins" J. Controlled Release 46 (1997) 165–175.

Molecular probes catalog, Set 33 Phospholipids 237–248, Molecular Probes Inc. (1995/1996).

What is claimed is:

1. A competition assay method for assaying an analyte in a sample, said analyte being a compound capable of binding to a receptor, and being neither an antibody nor an enzyme, said method comprising the elements of:

a) contacting the sample with a receptor preparation comprising solubilized receptor reconstituted into liposomes, the receptor preparation comprising a receptor specific to the analyte and comprising a detectable functionality wherein the sample contacting is effected under conditions resulting in binding of the receptor to the analyte if the analyte is present in the sample;

b) concomitantly with, or subsequently to, performing element a) contacting the sample with an immobilized ligand capable of binding with the receptor under conditions resulting in binding of the receptor to the ligand;

c) subsequently to performing elements a) and b), separating the resulting immobilized ligand-receptor phase from the receptor phase; and d) assaying the liposome detectable functionality to determine the presence or quantity of the analyte in the sample.

2. A method according to claim 1, wherein the detectable functionality is quantifiable by fluorescence detection, chemiluminescence detection or enzyme detection.

3. A method according to claim 1, wherein the immobilized ligand is coupled to a carrier via a spacer and said spacer comprises a carbon chain from 10 to 15 carbon atoms.

4. A method according to claim 1, wherein the analyte is detected at a level below about 100 nM.

5. A method according to claim 1, wherein the analyte is detected at a level below about 50 nM.

6. A method according to claim 1, wherein the receptor is a membrane-bound receptor capable of interacting with the analyte to yield a blocking or pharmacological response.

7. A method according to claim 1 wherein the receptor preparation comprises solubilized receptor, lipids promoting receptor-binding activity and, optionally, a fluorescent marker on the lipids.

8. A method according to claim 7 wherein the lipids comprise one or more lipids selected from the group consisting of phospholipids, glycolipids, cholesterol and apolectin.

9. A method according to claim 7 wherein the solubilized receptor is the product of fractionated homogenized tissue subjected to detergent solubilization and purification.

10. A method according to claim 1, wherein the detectable functionality is spectroscopically quantifiable wherein the receptor is a membrane-bound receptor capable of interacting with the analyte to yield a blocking or pharmacological response, wherein the receptor preparation comprises solubilized receptor and lipids promoting receptor-binding activity, the lipids comprising one or more lipids selected from the group consisting of phospholipids, glycolipids, cholesterol and apolectin and wherein the solubilized receptor is the product of fractionated homogenized tissue subjected to detergent solubilization and purification.

11. A method according to claim 1, wherein the receptor is present in step a) in a concentration between 1 pM–1 nM.

12. A method according to claim 1, wherein the detectable functionality in step a) is present in a concentration of 1 pM–1 pM.

13. A method according to claim 1, wherein the amount of immobilised ligand per assay, lies between 0.5 femtomole and 0.5 nanomole.

14. A method according to claim 1, wherein the detectable functionality is quantitated by spectroscopic techniques.

15. A method according to claim 1, wherein the detectable functionality comprises a labeled lipids.

16. A method according to claim 15, wherein the labeled lipid is selected from the group consisting of dansyl-DHPE, fluorescein DHPE and bodipy $FLC_5HPC$.

17. A method according to claim 1, wherein the detectable functionality is selected from the group consisting of luciferase, alkaline phosphatase and monoamine oxidase.

18. A method according to claim 1, wherein the immobilised ligand is a structurally related analogue of a compound with affinity for the receptor and is coupled via a spacer arm to the surface of a carrier material.

19. A method according to claim 18, wherein the spacer comprises a carbon chain of from 5 to 20 carbon atoms.

20. A method according to claim 1, wherein the ligand is a benzodiazepine derivative.

21. A method according to claim 1, wherein the analyte is detected at a level below 1 $\mu$M.

22. A method according to claim 1, wherein the receptor is a membrane-bound receptor.

23. A method according to claim 1, wherein the receptor comprises a membrane-bound receptor, selected from the group consisting of adenosine, adrenergic, dopamine, histamine, muscarinic, acetylcholinergic, nicotinic, opiate, serotonin, benzodiazepine, GABA, glycine, calcium channel, sodium channel, chemotactic peptide, epidermal growth factor, glucocorticoid, cannabinoid, cholecystokinin, cytokines, leuktriene and neurokinin receptors.

24. A method according to claim 23, wherein the receptor of interest is a benzodiazepine receptor.

25. A method according to claim 1, wherein the receptor comprises a soluble receptor consisting of steroid hormone receptors, androgen, estrogen and progesterone receptors.

26. A kit for carrying out a method according to claim 1, the kit comprising:

e) the ligand immobilised on a carrier or components for preparing the ligand immobilised on the carrier; and f) a receptor preparation comprising solubilized receptor reconstituted into liposomes or components for preparing the receptor preparation.

27. A kit according to claim further comprising one or more components selected from the group consisting of one or more reagents for performing the assay, a calibration standard and a quality control sample.

28. A kit according to claim 26, wherein the receptor preparation comprises lipids promoting receptor-binding activity.

29. A kit according to claim 26, wherein the reconstituting of the receptor-containing liposome employs lipids promoting receptor-binding activity.

30. A kit according to claim 4, comprising a detectable functionality incorporated in the receptor-containing liposome.

* * * * *